(12) United States Patent
Pinkos

(10) Patent No.: US 6,194,624 B1
(45) Date of Patent: Feb. 27, 2001

(54) HYDROGENATION OF POLYENES TO MONOENES

(75) Inventor: Rolf Pinkos, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/444,316

(22) Filed: Nov. 22, 1999

(30) Foreign Application Priority Data

Dec. 9, 1998 (DE) .............................................. 198 56 862

(51) Int. Cl.$^7$ ........................................................ C07C 5/02
(52) U.S. Cl. ............................................ 585/273; 585/277
(58) Field of Search ..................................... 585/273, 277

(56) References Cited

U.S. PATENT DOCUMENTS

| B 316,917 | 1/1975 | Fahey . |
| 3,804,914 | 4/1974 | Fahey . |
| 5,128,296 | 7/1992 | Matson et al. . |
| 5,177,278 | 1/1993 | Sanchez . |
| 5,180,870 | 1/1993 | Paciello . |
| 5,210,349 | 5/1993 | Matson et al. . |
| 5,321,176 | 6/1994 | Sanchez . |

OTHER PUBLICATIONS

D.R. Fahey, J. Org. Chem., vol. 38, No. 1, pp. 80–87, "Selective Hydrogenation of 1,5,9–Cyclododecatriene To Cyclododecene Catalyzed By Ruthenium Complexes", 1973.

*Primary Examiner*—Bekir L. Yildirim
(74) *Attorney, Agent, or Firm*—Oblon, Spivak, McClelland, Maier & Neustadt, P.C.

(57) ABSTRACT

A process for hydrogenating polyenes, especially 1,5,9-cyclododecatriene, to the corresponding monoenes, especially cyclododecene, using homogeneous ruthenium catalysts comprises hydrogenating in the presence of a carboxylic acid, advantageously a $C_1$–$C_{20}$ monocarboxylic acid, a $C_2$–$C_6$ dicarboxylic acid, cyclohexylcarboxylic acid, benzoic acid, terephthalic acid, phthalic acid or phenylacetic acid, especially acetic acid, propionic acid, succinic acid or adipic acid or a $C_{12}$–$C_{20}$ fatty acid.

The homogeneous ruthenium catalyst is advantageously generated in situ prior to the hydrogenation. The in situ generation is carried out in the additional presence of CO or formaldehyde and the hydrogenation in the additional presence of triphenylphosphine.

10 Claims, No Drawings

HYDROGENATION OF POLYENES TO MONOENES

SPECIFICATION

The present invention relates to a process for hydrogenating polyenes to monoenes using homogeneous ruthenium catalysts in the presence of carboxylic acids.

A main field of use for the process of the invention is the hydrogenation of 1,5,9-cyclododecatriene (CDT) to cyclododecene (CDE). CDE is useful, for example, as an intermediate for producing polyamide via 1,12-dodecanedioic acid, 1,12-diaminododecane and/or the lactam of 12-aminododecanoic acid. It may further be used as starting material for preparing scents such as 2-cyclododecyl-1-propanol, a sought-after musk scent.

A generally very important requirement of a hydrogenation of polyenes to the corresponding monoenes is that the yields of these reactions be very high, since the minimal mass and polarity differences between the reactants and the products mean that they are very difficult, if not impossible, to separate by distillation. That is, the polyene conversion has to be very high. It is customary to aim for yields above 98%.

U.S. Pat. No. 5,321,176, for example, describes the hydrogenation of polyenes to monoenes over homogeneous ruthenium catalysts in the presence of water. A CDT conversion of 98.4% is obtained in Example 2 after 4 hours (h) of reaction in the presence of water. The CDE yield is not disclosed. Example 1, which is carried out in the presence of somewhat less water, provides only an unsatisfactory conversion of 85.8% after 8 h of reaction. So the time required for quantitative conversion appears to fluctuate greatly with the process conditions, and consequently this process would not be simple to practice on an industrial scale since it does not guarantee consistently high CDE yields being obtained from quantitative conversion.

U.S. Pat. No. 5,180,870 describes a process for hydrogenating polyenes using homogeneous ruthenium catalysts in the presence of amines in the reaction mixture. None of the illustrative embodiments discloses how high CDE yields are to be obtained from quantitative conversion. In addition, with amines present, there must always be a chance of the product stream remaining contaminated with amines. Because of the intensive odors of most amines, this must be considered very problematical in relation to the production of scents in particular.

U.S. Pat. No. 5,177,278 discloses a CDT hydrogenation process using homogeneous ruthenium catalysts and a solvent selected from the group consisting of ethers or esters having a boiling point higher than 245° C. According to the illustrative embodiments, the best CDE selectivities range from 96 to 98%, but admittedly not in any case from quantitative conversion, so that the workup of the reaction mixture presents considerable separation problems. Moreover, hydrogenating in the presence of large solvent quantities diminishes the space-time yields, since the dilution uses up valuable reaction space. This disadvantageous effect likewise occurs in the processes of U.S. Pat. Nos. 3,804,914, 5,210,349 and 5,128,296, although fairly high CDE yields are obtained in some instances.

The process of the published patent application US B 316,917 is likewise conducted in solvents, and the maximum CDE yield is said to be about 95%. Conversion is incomplete, however.

D. R. Fahey in J. Org. Chem. 38 (1973), 80–87, describes the hydrogenation of CDT over various homogeneous ruthenium catalysts at great length. Again, all the examples are carried out in the presence of relatively large amounts of solvent. CDE yields of about 98% are reported. However, the reported use level of ruthenium is very high, based on CDT. This is because, after conversion of the units, it is found that 6 to 7 g of ruthenium (reckoned as metal) are used per 1 kg of CDT or CDE. Considering that 1 g of ruthenium costs about DM 2, the ruthenium costs alone of this process are about DM 12 to 14/kg of product. Therefore, an economical industrial process would require very frequent recycling of the catalyst. However, even practicing the process with recycling of the ruthenium catalyst customarily presents problems, such as changes to the catalyst, which then lead to reductions in the activity of the catalyst and hence in the selectivity. For example, oxidation of the catalyst by trace oxygen is likely.

It is an object of the present invention to provide a process whereby polyenes can be hydrogenated to the corresponding monoenes using homogeneous ruthenium catalysts whilst avoiding the disadvantages of the prior art processes, i.e., that the process shall be advantageously practicable even without use of large quantities of a costly catalyst and ideally without use of a solvent or at least with minimal solvent and yet consistently provides a very high yield from quantitative conversion.

We have found that, surprisingly, this object is achieved, i.e., polyenes are hydrogenated to the corresponding monoenes with complete conversion and high yields using homogeneous ruthenium catalysts, when the hydrogenation is carried out in the presence of carboxylic acids.

This invention accordingly provides a process for hydrogenating polyenes to the corresponding monoenes using homogeneous ruthenium catalysts, which comprises effecting said hydrogenation in the presence of a carboxylic acid.

It is very surprising that the presence of carboxylic acids prevents any significant further hydrogenation of the cyclododecene.

Examples of useful polyenes are cyclic polyenes such as 1,5,9-cyclododecatriene, 2,4-dimethylcyclododecatriene, 4-n-butylcyclododecatriene, 1-cyclohexyldodecatriene, 1-phenylcyclododecatriene, 1,5-cyclooctadiene, cyclooctatetraene, bicyclo [2.2.1]hepta-2,5-diene and bicyclo [2.2.2]octa-2,5-diene. Preference is given to 1,5,9-cyclododecatriene and 1,5-cyclooctadiene, especially 1,5,9-cyclododecatriene.

Operable ruthenium catalysts include for example those described in the above-cited references U.S. Pat. Nos. 5,180,870, 5,321,179, 5,177,278, 3,804,914, 5,210,349, 5,128,296, U.S. Pat. No. B 316,917 and by D. R. Fahey in J. Org. Chem. 38 (1973), 80–87. The preferred catalysts are $(TPP)_2(CO)_2RuCl_2$ and the corresponding chlorine-free variants. TPP is triphenylphosphine.

Since the catalyst is formed in situ in a preferred embodiment of the invention, it is believed that mixtures of ruthenium compounds are present. Active catalyst complexes are likely to be present in hydride form in these mixtures. Examples of suitable starting compounds for forming the catalyst in situ include ruthenium chloride, ruthenium acetate, ruthenium acetylacetonate or other commercially available ruthenium compounds.

As well as a ruthenium component, the reaction mixture customarily further includes $NR_3$, $PR_3$, $AsR_3$ or $SbR_3$, where R is alkyl and/or aryl. Preference is given to using triphenylphosphine in addition to the ruthenium component.

The process of the invention utilizes from 0.1 to 2000 mg, preferably from 1 to 1000 mg, especially from 10 to 200 mg of ruthenium (reckoned as metal) per 1 kg of polyene. This results in such low catalyst costs that the catalyst need not necessarily be recycled. However, the catalyst may well be recycled, in which case the presence of the carboxylic acid has a stabilizing effect on the catalyst. Repeated use of the catalyst does not diminish its activity or selectivity.

Examples of useful carboxylic acids are aliphatic, cycloaliphatic, aromatic or araliphatic carboxylic acids. Preference is given to using those which are soluble in the reaction system under the reaction conditions. Examples of suitable carboxylic acids are $C_1$–$C_{20}$ monocarboxylic acids, $C_2$–$C_6$ dicarboxylic acids, cyclohexylcarboxylic acid, benzoic acid, terephthalic acid, phthalic acid and phenylacetic acid. Particularly preferred acids are aliphatic mono- and dicarboxylic acids, especially acetic acid, propionic acid, and also $C_{12}$–$C_{20}$ fatty acids, succinic acid and adipic acid.

The amount of carboxylic acid added per kg of polyene is generally within the range from 0.001 to 100 g, preferably within the range from 0.01 to 50 g, especially within the range from 0.05 to 25 g.

A CO source is additionally included when the catalyst is to be formed in situ. This CO source may either be gaseous CO itself or else formaldehyde.

The process of the invention is generally carried out at from 50 to 300° C., preferably from 80 to 250° C., especially from 100 to 200° C. The reaction pressures are generally within the range from 1 to 300 bar, preferably within the range from 1 to 200 bar, especially within the range from 1 to 100 bar.

The time of reaction per batch and the residence time in the case of a continuous process are generally within the range from 0.5 to 48 hours. They depend essentially on the batch size and on the means for supplying or removing energy. Owing to the presence of carboxylic acids in the reaction mixture, it does not matter if the reaction batch is handled for longer than necessary under the reaction conditions. This permits an appreciably simplified process management and monitoring system.

The Examples which follow illustrate the process of the invention.

EXAMPLE 1

A 2.5 l stirred autoclave was charged with 1 kg of trans-, trans-, cis-1,5,9-cyclododecatriene (from Sigma-Aldrich, D-89555 Steinheim), 150 mg of $RuCl_3*H_2O$, 20 g of triphenylphosphine, 12.5 g of 37% strength aqueous formaldehyde solution, 25 ml of ethanol and 2.5 g of acetic acid. The reactor was purged with nitrogen or hydrogen, and 15 bar of hydrogen were injected. Thereafter the reactor was heated up with stirring. At about 130° C., the reactor pressure decreased markedly and an exothermic reaction kicked in, taking the temperature up to 163° C. The temperature was subsequently maintained between 140 and 150° C. by injecting more hydrogen a little at a time. The maximum pressure was 20 bar. After the uptake of hydrogen had ceased, the reaction effluent was found to contain 98.1% of cyclododecene and 1.8% of cyclododecane by gas chromatography (GC). The yield was accordingly 98.2% of theory.

EXAMPLE 2

A 70 ml autoclave equipped with a magnetic stirrer was charged with 40 g of trans-, trans-, cis-1,5,9-cyclododecatriene, 50 mg of $RuCl_3*H_2O$, 400 mg of triphenylphosphine, 0.5 g of 37% strength aqueous formaldehyde solution and 100 mg of acetic acid. The reactor was purged with nitrogen and hydrogen and then brought to a hydrogen pressure of 20 bar and heated up with stirring. At 115° C., the reactor pressure decreased noticeably and the internal temperature rose quickly to 140° C. Thereafter the reactor was constantly maintained at 20 bar and 145° C. by means of hydrogen. After about 2.5 hours the reactor was cooled down and decompressed. The effluent was found by GC to contain a yield of 97% of cyclododecene and 1.8% of cyclododecane. The remainder was cyclododecadiene.

COMPARATIVE EXAMPLE

Example 2 was repeated without acetic acid, affording a yield of only 86.8% of cyclododecene and of 13.2% of cyclododecane (GC analysis of effluent).

What is claimed is:

1. A process for hydrogenating polyenes to the corresponding monoenes using homogeneous ruthenium catalysts, which comprises effecting said hydrogenation in the presence of a carboxylic acid.

2. A process as claimed in claim 1, wherein the homogeneous ruthenium catalyst is generated in situ prior to said hydrogenation.

3. A process as claimed in claim 1, wherein the catalyst is generated in situ in the presence of CO or formaldehyde prior to said hydrogenation.

4. A process as claimed in claim 1, wherein said hydrogenation is effected in the presence of triphenylphosphine.

5. A process as claimed in claim 1, wherein said hydrogenation is effected at from 50 to 300° C. and at from 1 to 300 bar.

6. A process as claimed in claim 1, wherein the polyene used is 1,5,9-cyclododecatriene.

7. A process as claimed in claim 1, wherein the polyene used is a cyclooctadiene.

8. A process as claimed in claim 1, wherein from 0.1 to 2000 mg of ruthenium (reckoned as metal) is used per kg of polyene.

9. A process as claimed in claim 1, wherein the carboxylic acid used is a $C_1$–$C_{20}$ monocarboxylic acid, a $C_2$–$C_6$ dicarboxylic acid, cyclohexylcarboxylic acid, benzoic acid, terephthalic acid, phthalic acid or phenylacetic acid.

10. A process as claimed in claim 1, wherein the carboxylic acid used is acetic acid, propionic acid, succinic acid or adipic acid or a $C_{12}$–$C_{20}$ fatty acid.

* * * * *